(12) United States Patent
Oh

(10) Patent No.: US 11,376,194 B2
(45) Date of Patent: Jul. 5, 2022

(54) INFUSION SYSTEM

(71) Applicant: Oh Pharmaceutical Co., Ltd., Crown Point, IN (US)

(72) Inventor: Gibum Oh, Seoul (KR)

(73) Assignee: OH PHARMACEUTICAL CO., LTD., Oak Brook, IL (US)

( * ) Notice: Subject to any disclaimer, the term of this patent is extended or adjusted under 35 U.S.C. 154(b) by 82 days.

(21) Appl. No.: 16/330,206

(22) PCT Filed: Sep. 24, 2018

(86) PCT No.: PCT/US2018/052425
§ 371 (c)(1),
(2) Date: Mar. 4, 2019

(87) PCT Pub. No.: WO2020/068031
PCT Pub. Date: Apr. 2, 2020

(65) Prior Publication Data
US 2020/0170883 A1 Jun. 4, 2020

(51) Int. Cl.
*A61J 1/20* (2006.01)
*A61J 1/14* (2006.01)
*A61J 1/18* (2006.01)
*A61K 45/06* (2006.01)
*A61J 1/06* (2006.01)
*A61J 1/10* (2006.01)

(52) U.S. Cl.
CPC ............ *A61J 1/201* (2015.05); *A61J 1/1431* (2015.05); *A61J 1/1462* (2013.01); *A61J 1/1475* (2013.01); *A61J 1/18* (2013.01); *A61J 1/2089* (2013.01); *A61K 45/06* (2013.01); *A61J 1/065* (2013.01); *A61J 1/067* (2013.01); *A61J 1/10* (2013.01); *A61J 1/2096* (2013.01)

(58) Field of Classification Search
CPC .. A61J 1/20; A61J 1/2065; A61J 1/2089; A61J 1/2003; A61J 1/201; A61J 1/18; A61J 1/2048; A61J 1/00; C12Q 1/22
See application file for complete search history.

(56) References Cited

U.S. PATENT DOCUMENTS

| | | | |
|---|---|---|---|
| 4,467,588 A | 8/1984 | Carveth | |
| 4,936,841 A * | 6/1990 | Aoki | A61J 1/2089 604/413 |
| 5,308,347 A | 5/1994 | Sunago et al. | |
| 5,352,191 A | 10/1994 | Sunago | |

(Continued)

OTHER PUBLICATIONS

Master UK. How to use UK Injection Kit. YouTube [online] [video], Nov. 22, 2017 [retrieved Jan. 23 on Jan. 4, 2019], Retrieved from <https://www.youtube.com/watch?v=6NlqeaGOmg8>.

(Continued)

*Primary Examiner* — Tatyana Zalukaeva
*Assistant Examiner* — Meagan Ngo
(74) *Attorney, Agent, or Firm* — Lucas & Mercanti, LLP

(57) ABSTRACT

The present invention provides an integrated infusion system having a drug vial container adapted to hold a drug vial, the drug vial container having a drug vial holder element and a holder cap element, wherein the drug vial holder element and the holder cap element are fused together forming a seal; and a chemical indicator inside the drug vial container for sterility verification.

12 Claims, 16 Drawing Sheets

(56) References Cited

U.S. PATENT DOCUMENTS

| | | | | |
|---|---|---|---|---|
| 5,380,315 | A | * | 1/1995 | Isono ............... A61J 1/2089 |
| | | | | 604/403 |
| 5,405,580 | A | * | 4/1995 | Palmer ............... A61L 2/28 |
| | | | | 206/569 |
| 5,826,713 | A | | 10/1998 | Sunago et al. |
| 9,421,148 | B2 | | 8/2016 | Oh |
| 2013/0102990 | A1 | | 4/2013 | Domkowski |
| 2013/0218122 | A1 | * | 8/2013 | Oh ............... A61K 31/397 |
| | | | | 604/414 |
| 2013/0340891 | A1 | * | 12/2013 | Steube ............... A61J 1/20 |
| | | | | 141/329 |
| 2016/0000650 | A1 | | 1/2016 | Gobbi |
| 2016/0262981 | A1 | * | 9/2016 | Carrez ............... A61J 1/1406 |

OTHER PUBLICATIONS

International Search Report and Written Opinion for Corresponding International Application No. PCT/US2018/52425 (7 Pages) (Jan. 29, 2019).

* cited by examiner

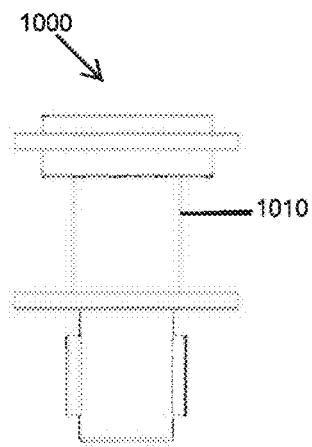
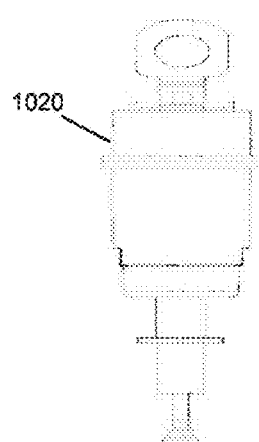
FIG 1A  FIG 1B  FIG 1C
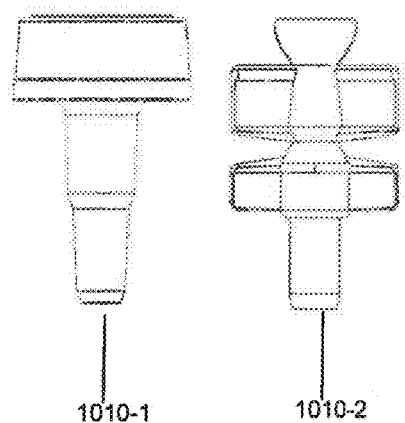
FIG 1D

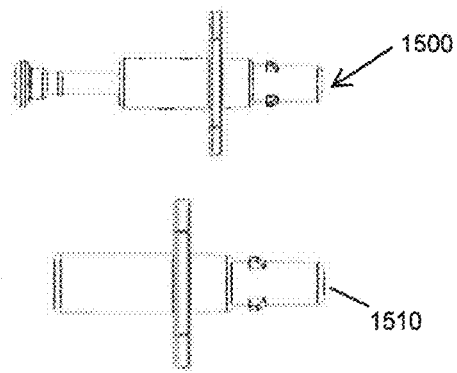
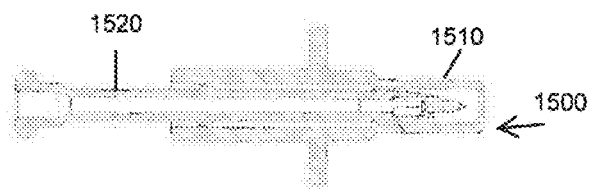
FIG 6B
FIG 6A
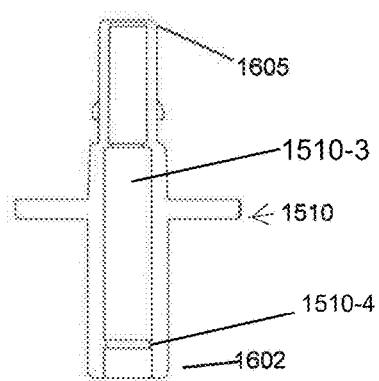
FIG 7A
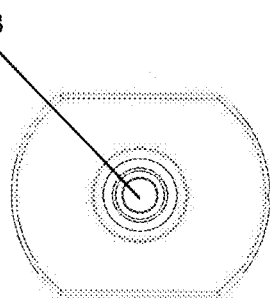
FIG 7B     FIG 7C
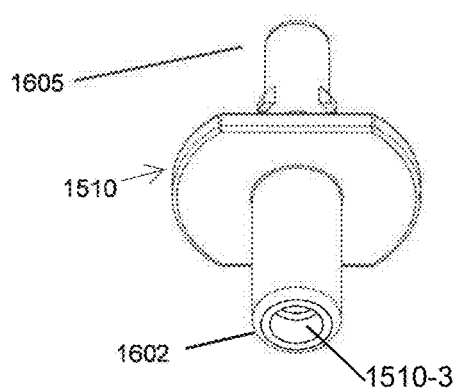
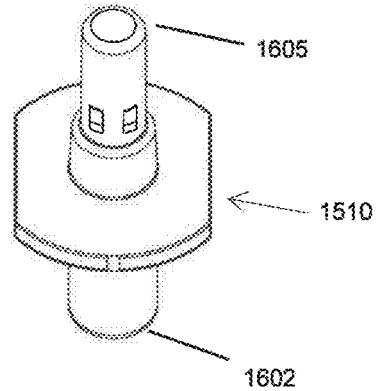
FIG 7D     FIG 7E

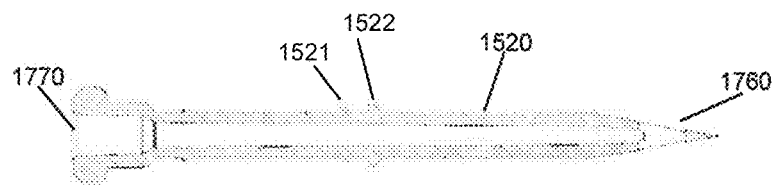
FIG 8A
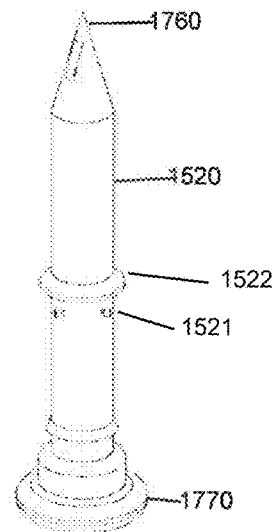
FIG 8B
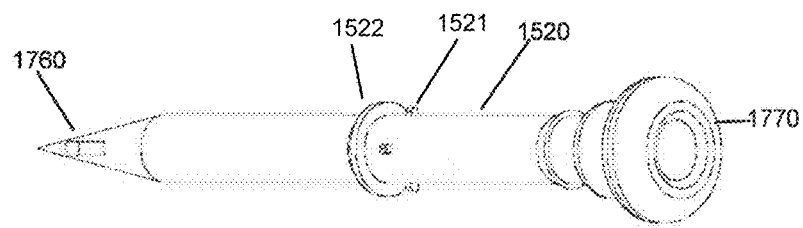
FIG 8C
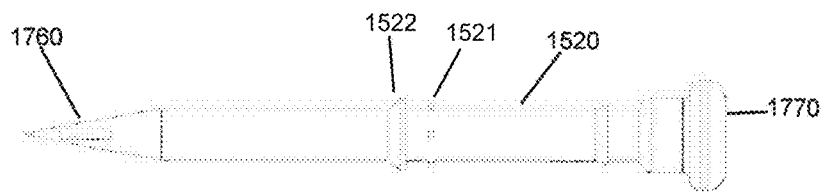
FIG 8D
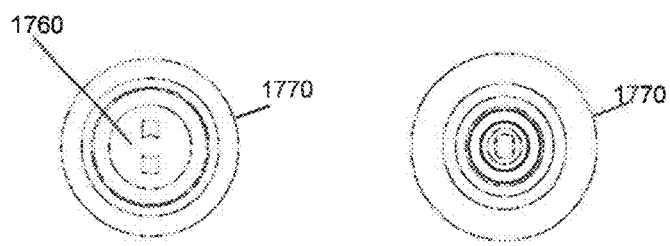
FIG 8E     FIG 8F

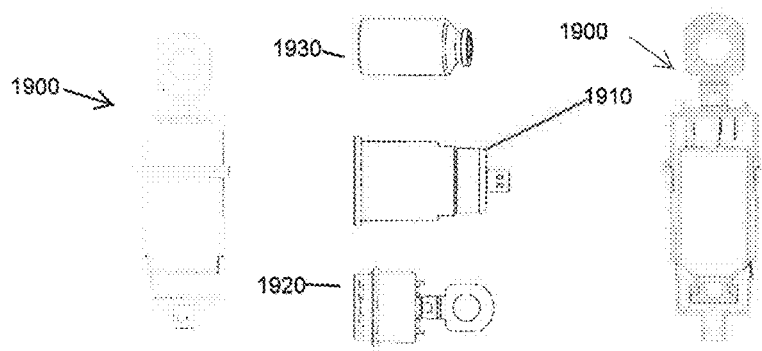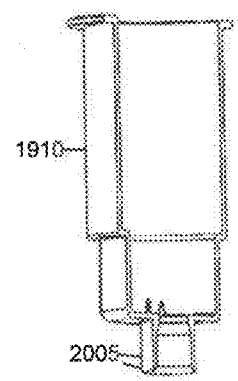
FIG 10  FIG 11C
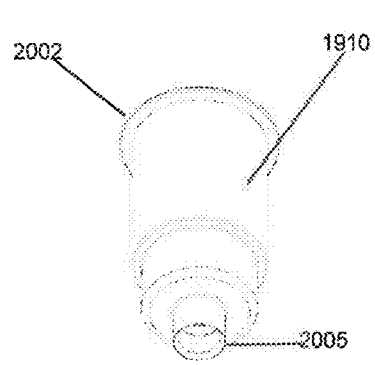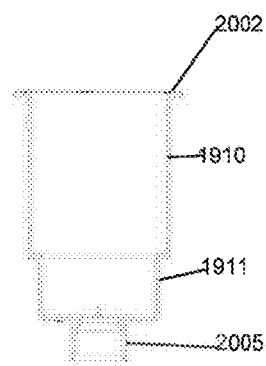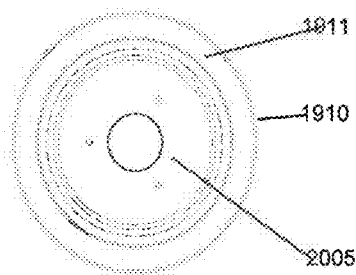
FIG 11A  FIG 11D  FIG 11F
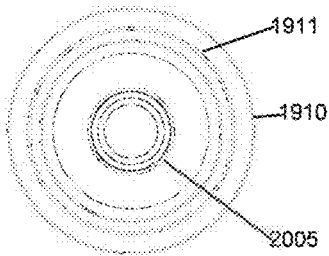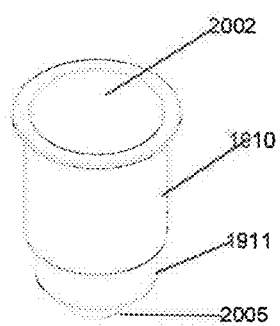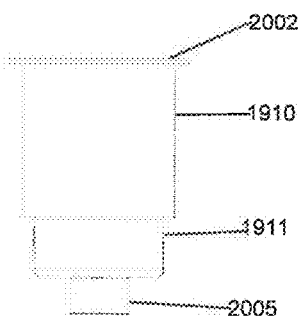
FIG 11B  FIG 11E  FIG 11G

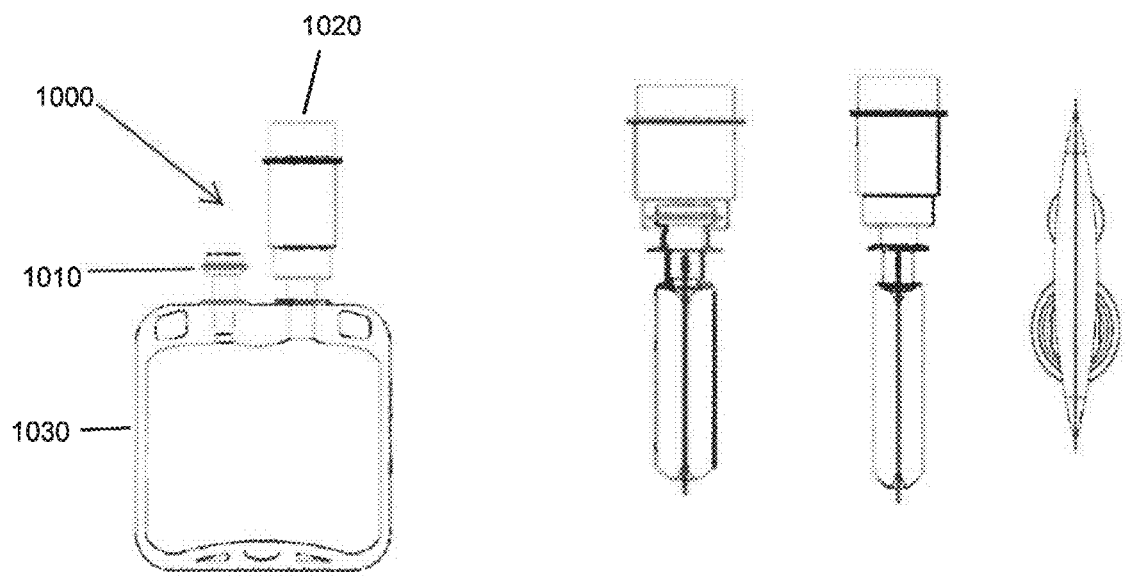
FIG 15A
FIG 15B
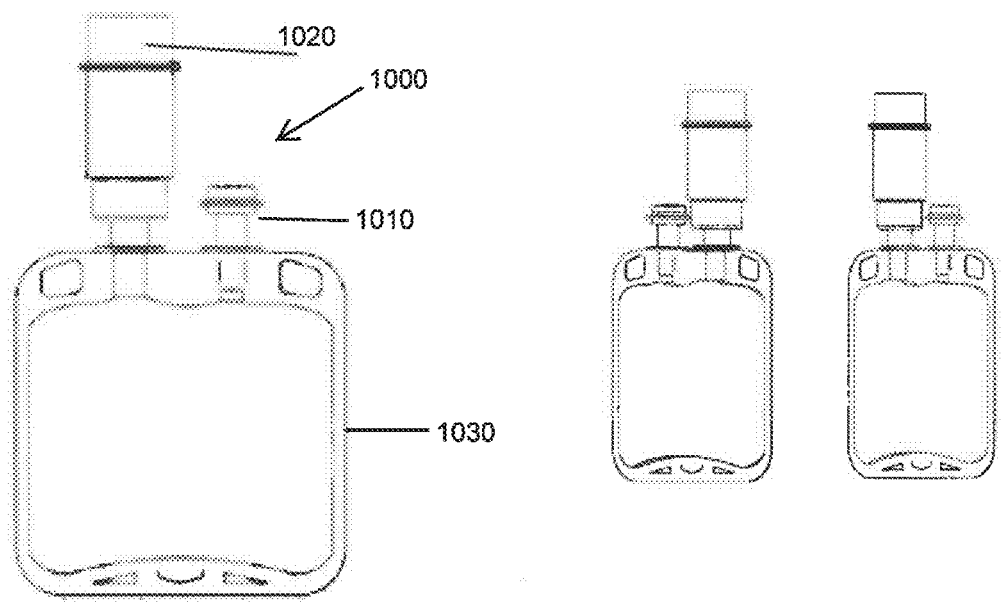
FIG 15C

INFUSION SYSTEM

CROSS-REFERENCE TO RELATED APPLICATION

This application is a 371 of PCT/US2018/52425, filed Sep. 24, 2018, the contents of which is incorporated herein by reference.

TECHNICAL FIELD

The present invention relates to an integrated infusion system having an integral structure where a powdered, freeze-dried or liquid medicine container is easily connected with a container including a solution in a completely sterilized state so that the powdered, freeze-dried or liquid medicine in the medicine container is mixed with the solution in the container with one touch to be readily available within a short time.

BACKGROUND OF THE INVENTION

When administering powdered form or lyophilized (powder) form of an anticancer medicine or a freeze-dried medicine to a patient in a clinic or a hospital, the powdered medicine which is included in a container like a vial is mixed with a certain amount of solution like saline and then it is instilled.

For instillation, a solution like saline solution is injected into a vial with a disposable syringe to dissolve the powered medicine, thereafter the dissolved solution is transferred to the solution container with another disposable syringe. This method is generally used because it does not need additional equipment. However, impurities may infiltrate during the process and this poses a great disadvantage and danger to the patient being treated.

Another process of administration of the powdered form or lyophilized medicine uses a system where the dissolved medicine is coupled with the container including the solution using a coupling tool such as a double-ended needle or a coupling tube. The container including the dissolved medicine is inclined so that the medicine dissolved in the container is inserted into the container including the solution.

However, such operation is complicated and time-consuming. Particularly, since the process of perforating a hole on the container including the medicine is carried out in the air, and the possibilities of contaminating the medicine is increased. Moreover, the possibility of a nosocomial infection due to an abuse of antibiotic injection is also increased.

Accordingly, there is still a need for a system where the powdered, freeze-dried or liquid medicine in the medicine container which can be mixed with the solution in the solution container in one step, in a visually confirmed sterile environment, to be readily available for application within a short period of time.

SUMMARY OF THE INVENTION

The present invention provides an integrated infusion system comprising a drug vial container adapted to hold a drug vial, the drug vial container comprising a drug vial holder element and a holder cap element, wherein the drug vial holder element and the holder cap element are fused together forming a seal; a hydrogen chemical indicator inside the drug vial container for sterility verification; a second container adapted to hold a liquid, the second container including a first end and a second end; a fused or sealed connection port connecting the second container and the drug vial container, the fused or sealed connection port having a cavity, the cavity having a protruding section functioning as a stopper; a releasing member disposed at the second end of the second container, the releasing member adapted to release the liquid from the second container; a flue needle comprising a seat and a point, wherein the point of the flue needle is adapted to enter the cavity of the fused connection port and perforate the drug vial in response to a pressure applied on the seat of the flue needle; at least three interrupting protuberances on the flue needle, the interrupting protuberances being configured for easy insertion and for preventing the flue needle from retracting after the pressure is applied on the seat of the flue needle perforating the drug vial; at least one fixing protuberance on the flue needle adapted to contact and interact with the protruding section inside the cavity of the fused connection port and preventing the flue needle from moving from an initial position in the absence of an external force.

BRIEF DESCRIPTION OF THE DRAWINGS

FIGS. 1A-1D show an integrated infusion system with some of its components in accordance with the invention.

FIGS. 6A-6B show components of a connection port assembly in accordance with the invention.

FIGS. 7A-7K show a connection port in accordance with the invention.

FIGS. 8A-8F show a flue needle in accordance with the invention.

FIG. 10 shows components of a vial holder assembly in accordance with the invention.

FIGS. 11A-11G show a vial holder in accordance with the invention.

FIGS. 15A-15C show an integrated infusion system in an assembled configuration in accordance with the invention.

DETAILED DESCRIPTION OF THE INVENTION

Figure 2A:
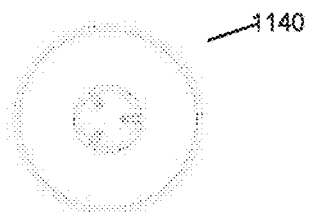
FIGS. 2A-2H show components of a releasing member in accordance with the invention.
Figure 2B:
Figure 2C:
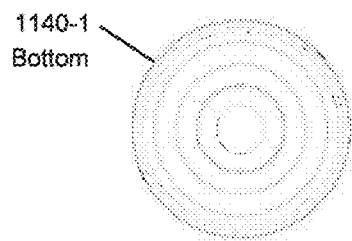
Figure 2D:
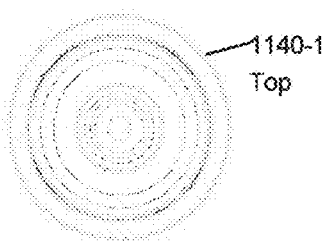
Figure 2E:
Figure 2F:
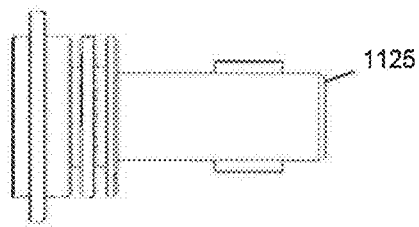
Figure 2G:
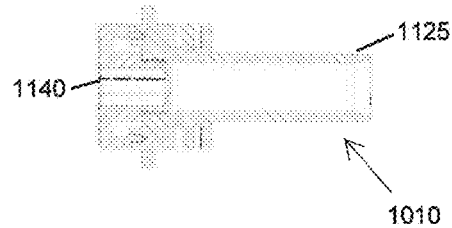
Figure 2H:
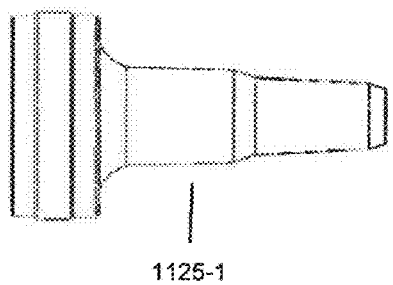
Figure 3A:
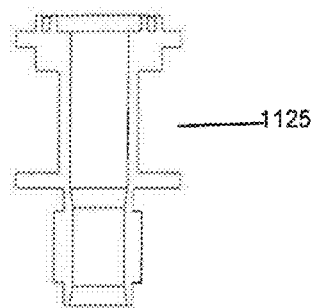
FIGS. 3A-3G show an infusion port in accordance with the invention.
Figure 3C:
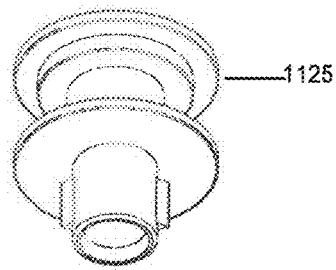
Figure 3E:
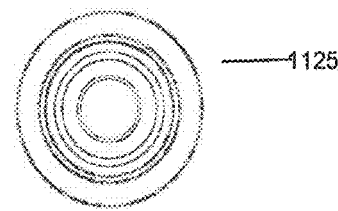
Figure 3B:
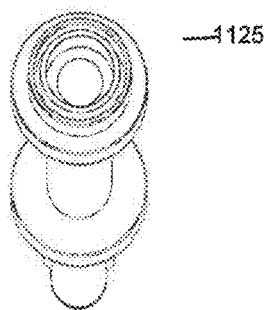
Figure 3D:
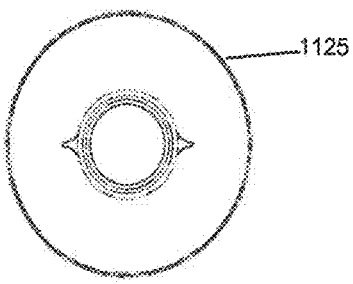
Figure 3F:
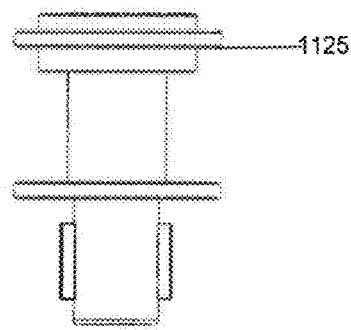
Figure 3G:
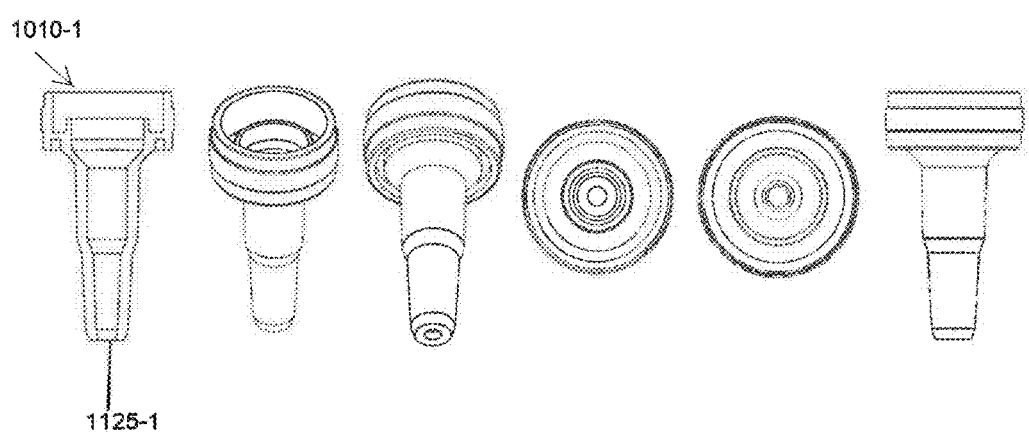
Figure 4A:
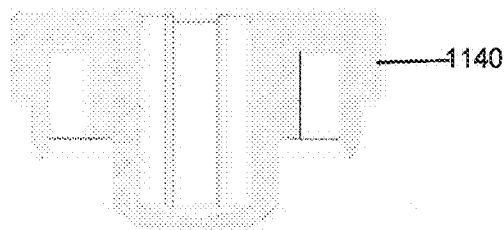
FIGS. 4A-4G show a cap in accordance with the invention.
Figure 4D:
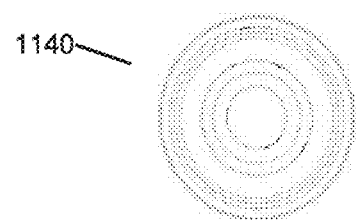
Figure 4B:
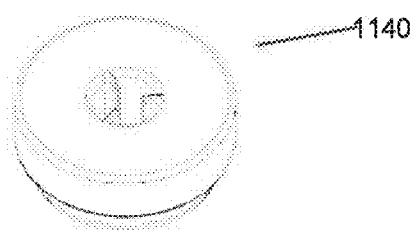
Figure 4E:
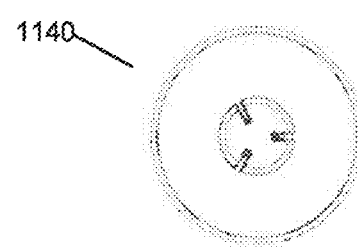
Figure 4C:
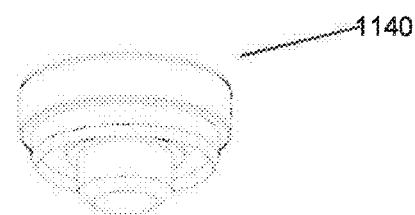
Figure 4F:
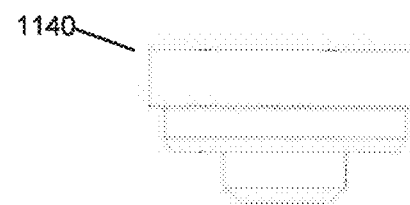
Figure 4G:
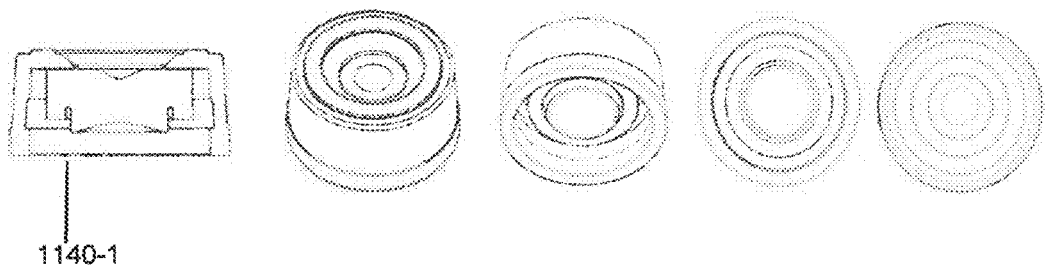
Figure 5A:
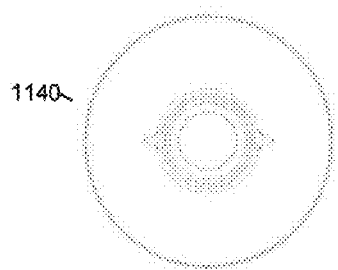
FIGS. 5A-5F show an infusion port and cap in an assembled configuration in accordance with the invention.
Figure 5C:
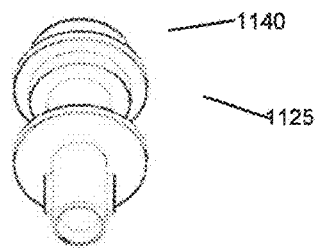
Figure 5E:
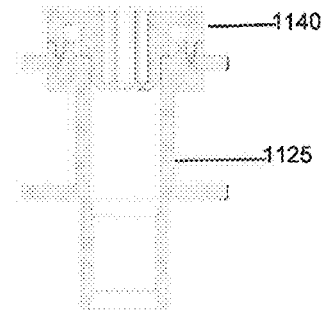
Figure 5B:
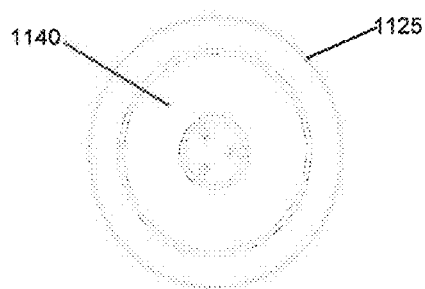
Figure 5D:
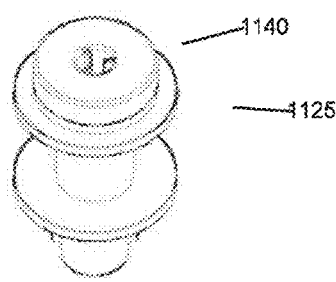
Figure 5F:
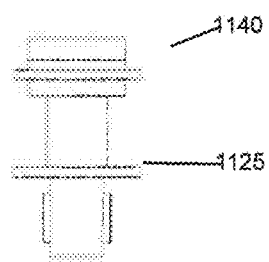
Figure 7F:
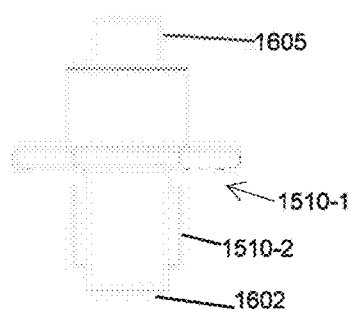
Figure 7H:
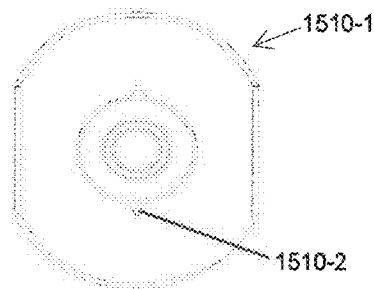
Figure 7J:
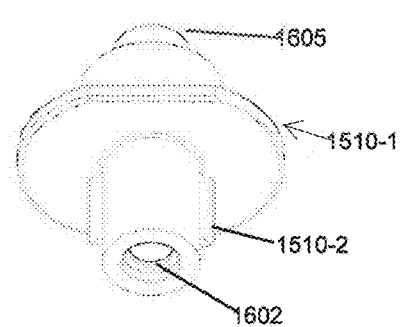
Figure 7G:
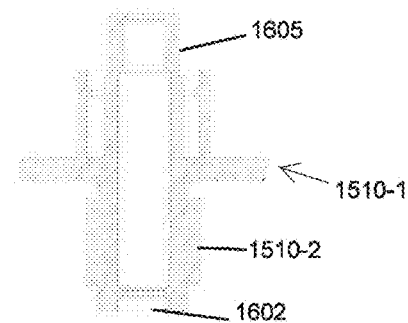
Figure 7I:
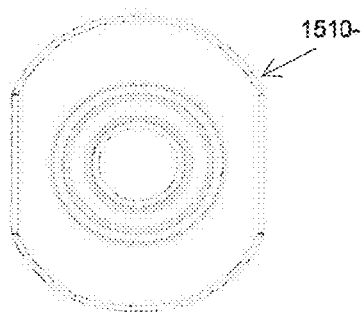
Figure 7K:
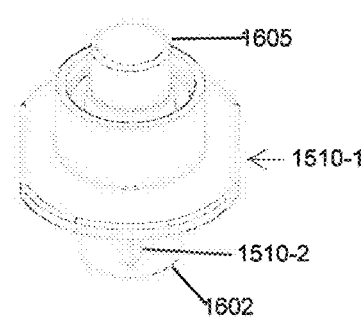
Figure 9A:
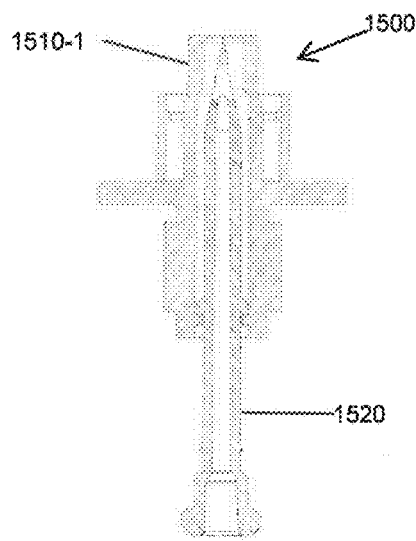
FIGS. 9A-9F show a connection port assembly including the connection port and a flue needle in an assembled configuration in accordance with the invention.
Figure 9B:
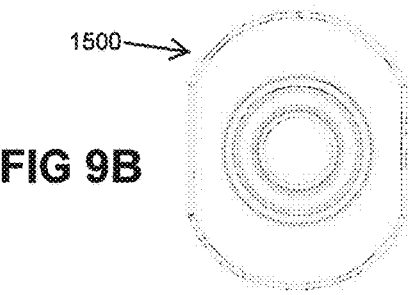
Figure 9C:
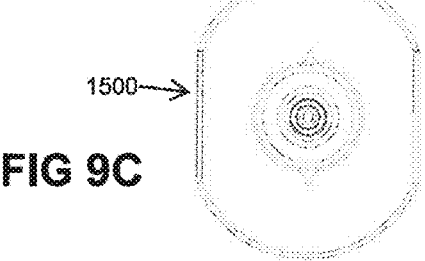
Figure 9D:
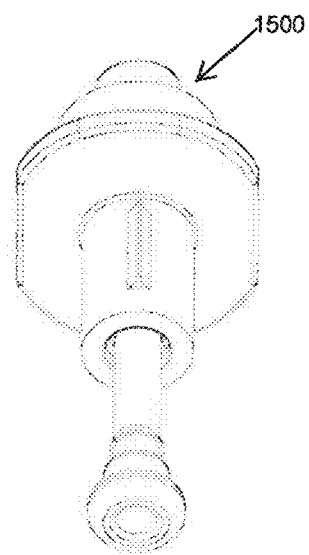
Figure 9E:
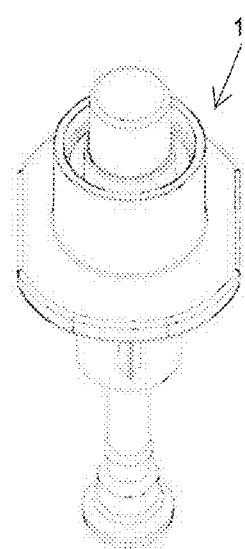
Figure 9F:
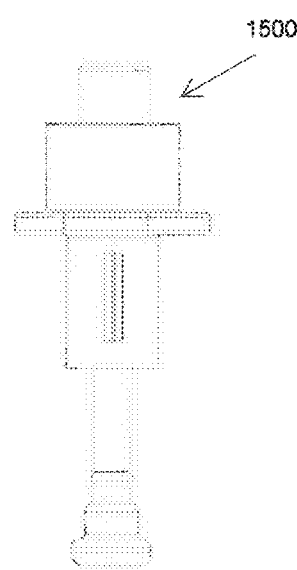

The present invention provides an integrated infusion system comprising a drug vial container containing a drug vial, a second container holding a liquid and a flue needle travelling through one end of the second container to the drug vial container in order to perforate the drug vial.

A fused connection port connects the second container with the drug vial container. The fused connection port prevents any contact with the external environment, thereby maintaining a sterile environment inside the drug vial container and inside the second container holding the liquid.

The fused connection port has a cavity and integral to the shape of this cavity is an internally protruding section (1510-4) which functions as a stopper for the flue needle. This protruding section (1510-4) is part of the shape or structure of the cavity (1510-3) of the fused connection port. See FIG. 16B. The protruding section may also control the forward movement of the flue needle.

The function of the connection port's cavity as a stopper for the flue needle and/or the controlling of the forward movement of the flue needle works in connection with the flue needle's design. The flue needle comprises a seat and a point, wherein the point of the flue needle is adapted to enter the cavity of the fused connection port and perforate the drug vial in response to a pressure applied on the seat of the flue needle.

There is at least one fixing protuberance (1522) on outer perimeter of the flue needle, adapted to contact and interact with the protruding section inside the cavity of the fused connection port and preventing the flue needle from moving from an initial position in the absence of an external force.

Additionally, there are at least two or three interrupting protuberances (1521) on the outer perimeter of the flue needle, the interrupting protuberances being configured for easy insertion and for preventing the flue needle from retracting after the pressure applied on the seat of the flue needle has perforated the drug vial. Moreover, the flue needle is characterized in that at least one interrupting protuberance is formed at a position on its outer perimeter so that it stops at a predetermined position in the coupling member after it is moved so as to not be displaced any further.

The flue needle is a cavity needle having at least one passage through which a liquid medicine flows.

The flue needle is also characterized in that at least one fixing protuberance is formed at a position on its outer perimeter so that it is not easily displaced from the initial state without an external force.

In one embodiment, the flue needle may also include a marker near the seat of the needle, as a visual confirmation of when the needle enters the cavity of the fused connection port and perforates the drug vial in response to the pressure applied on the seat of the flue needle. The marker will facilitate the operator to visually confirm that the needle has been correctly inserted and at a predetermined length of the needle. The marker on the needle can be in the form of a marking on a predetermined length on the needle itself. The marking on the needle can also be displayed in colors. For example, a black line or colored line may appear on the outer perimeter of the needle at a predetermined length from the seat.

In another embodiment, the flue needle itself may be of a color such that the operator will of the syringe will readily confirm visually that the needle has been correctly inserted when the color of the needle is seen through the device according to the invention.

Inside the drug vial container there is a hydrogen peroxide chemical indicator. The hydrogen peroxide chemical indicator inside the drug vial container can be, for example, inserted and VHP (Vapor Hydrogen Peroxide) performed for sterilization. The internal sterility can be verified through the change in color of the indicator inside the drug vial container. For example, the indicator changes from pink to purple if the interior is no longer a sterile environment.

Additionally, the drug vial container comprises a drug vial holder element and a holder cap element wherein the drug vial holder element and the holder cap element are fused together forming a seal. The drug vial holder element and the holder cap element can be fused together via ultrasonic or heat fusion or any other conventional means. Such design further aids in the maintenance of a sterile environment for the inventive integrated infusion system.

The holder cap may optionally have a fixing packing element for holding the medicine container in place. Moreover, the holder cap element may also have a hanging means for hanging a medicine bottle.

However, a packing element, such as rubber, is not necessary at the tip of the drug vial holder in order to secure the drug vial in place for protecting the integrity of the entry point of the drug vial because of the fused connection port which maintains it sterile and also because of the slimmer neck design portion which holds the drug vial in place.

In addition, the drug vial container may be of a glass or a plastic material.

The integrated infusion system according to the present invention can be manufactured easily and at a low cost because the whole system is compact and the number of the parts is extremely reduced without risking contamination from the outside environment affecting the entire system.

Moreover, the solution in the second container can easily move when the second container is a plastic container by using a flue needle, which is a cavity needle. The medicine in the drug vial container and the solution pouch can be mixed and be readily available within a short time.

FIG. 1 shows components of an integrated infusion system in accordance with the invention. FIGS. 1A, 1B and 1C show a syringe kit 1000 including a releasing member 1010, a connection port/vial holder apparatus 1020, and a pouch 1030. FIG. 1D shows an alternate shape of the releasing member, such as shown as 1010-1 and 1010-2.

FIG. 2 shows components of releasing member 1010 in accordance with the invention. Releasing member 1010 includes an infusion port 1125 (FIG. 2F) and a cap 1140 (FIGS. 2A and 2B) as shown in FIG. 2G. In FIG. 2H, alternative design of the infusion port 1125 is shown in a horizontal side view as 1125-1. Different views of alternative designs of the cap is also shown in FIGS. 2C, 2D and 2E as 1140-1.

FIG. 3 shows the infusion port 1125 in accordance with the invention. FIG. 3A shows a cross-sectional view of infusion port 1125. FIGS. 3B and 3C show perspective views of infusion port 1125. FIG. 3D shows a first end view of infusion port 1125. FIG. 3E shows a second end view of infusion port 1125. FIG. 3F shows a side view of infusion port 1125. FIG. 3G show several views of an alternative design of the releasing member 1010-1 with the infusion port 1125-1.

FIG. 4 shows the cap 1140 in accordance with the invention. FIG. 4A shows a cross-sectional view of cap 1140. FIGS. 4B and 4C show perspective views of cap 1140. FIG. 4D shows a first end view of cap 1140. FIG. 4E shows a second end view of cap 1140. FIG. 4F shows a side view of cap 1140. FIG. 4G shows different views of an alternative design of the cap 1140-1.

FIG. 5 shows the infusion port 1125 of FIGS. 3A, 3B, 3C, 3D, 3E and 3F and the cap 1140 of FIGS. 4A, 4B, 4C, 4D, 4E and 4F in an assembled configuration in accordance with the invention. Cap 1140 fits onto an end of infusion port 1125.

Connection port/vial holder apparatus 1020 includes a connection port assembly and a vial holder assembly. FIG. 6 shows components of a connection port assembly in accordance with the invention. Connection port assembly 1500 includes a connection port 1510 and a flue needle 1520. FIG. 6A shows connection port 1510 and flue needle 1520 separately, and FIG. 6B shows connection port 1510 and flue needle 1520 in an assembled configuration.

FIG. 7 shows connection port 1510 in accordance with the invention. Connection port 1510 has a cavity 1510-3, a receiving end 1602 adapted to receive a flue needle (such as flue needle 1520) and a connector end 1605. The connection port can optionally have ribs 1510-2. Ribs 1510-2 prevent films touching each other and making a pinhole during heat fusion. FIG. 7A shows a cross-sectional view of connection port 1510 and the cavity 1510-3. FIGS. 7B and 7C show first and second end views of connection port 1510 FIGS. 7D-7E show perspective views of connection port 1510. FIGS. 7F, 7G, 7H, 7I, 7J and 7K show different view of alternative designs of connection port 1510-1.

FIG. 8 shows flue needle in accordance with the invention having the interrupting protuberances (1521) and fixing protuberance (1522). FIG. 8A shows a cross-sectional view of flue needle 1520. Flue needle 1520 includes a point 1760 and an end 1770. FIGS. 8B and 8C show perspective views of flue needle 1520. FIG. 8D shows a side view of flue needle 1520. FIG. 8E shows an end view of flue needle 1520 (in which point 1760 is visible). FIG. 8F shows an end view of flue needle 1520 (in which end 1770 is visible).

FIG. 9 shows connection port assembly 1500, including a connection port 1510-1 and a flue needle 1520, in an assembled configuration in accordance with the invention. FIG. 9A shows a cross-sectional view of connection port assembly 1500. FIGS. 9B and 9C show end views of connection port assembly 1500. FIGS. 9D and 9E show perspective views of connection port assembly 1500. FIG. 9F shows a side view of connection port assembly 1500.

FIG. 10 shows components of a vial holder assembly 1900 in accordance with the invention. Components of vial holder assembly 1900 include a vial holder 1910, a holder cap 1920, and a medicine container 1930. Vial holder assembly 1900 is also shown in FIG. 10 in assembled form.

Drug vial container 1930 is adapted to hold a selected medicine. The drug vial container 1930 fits into and is held securely by drug vial holder 1910, which is designed with a slimmer neck area 1911.

FIG. 11 shows drug vial holder 1910 in accordance with the invention. FIG. 11A shows a perspective view of vial holder 1910. Vial holder 1910 has a container end 2002 adapted to receive a medicine container (such as medicine container 1930), and a connecting end 2005. FIG. 11B shows an end view of vial holder 1910. FIG. 11C shows a perspective view of a cross-section of vial holder 1910. FIG. 11D shows a side view of vial holder 1910. FIG. 11E shows a perspective view of vial holder 1910. FIG. 11F shows an end view of vial holder 1910. FIG. 11G shows a side view of vial holder 1910.

Figure 12A:
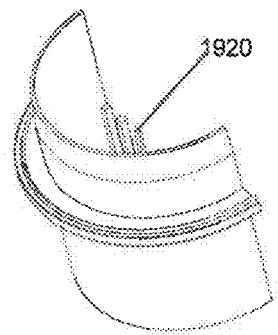
FIGS. 12A-12G show a holder cap in accordance with the invention.
Figure 12B:
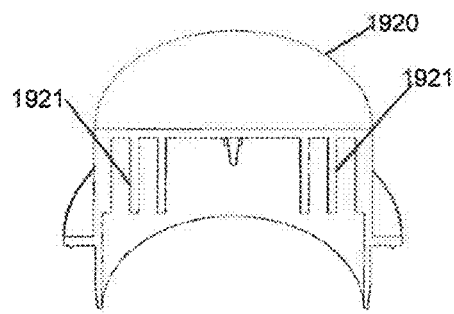
Figure 12C:
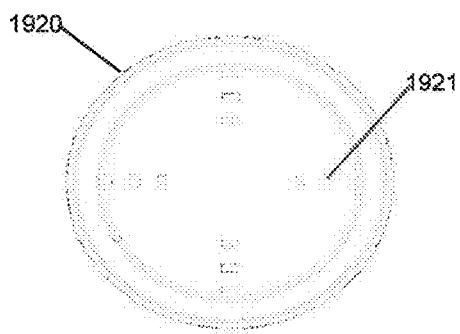
Figure 12D:
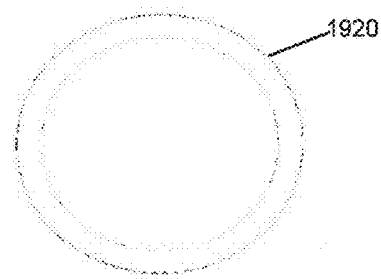
Figure 12E:
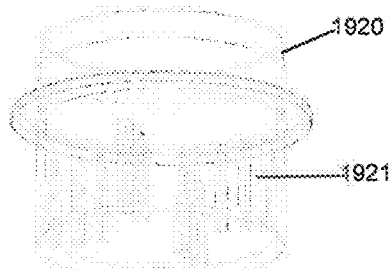
Figure 12F:
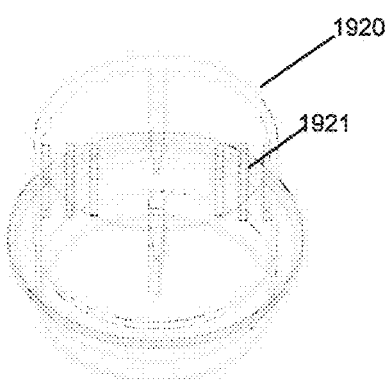
Figure 12G:
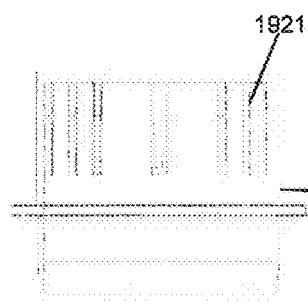
Figure 13A:
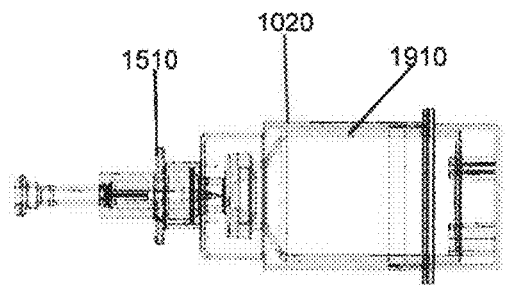
FIGS. 13A-13F show a connection port/vial holder apparatus in an assembled configuration in accordance with the invention.
Figure 13D:
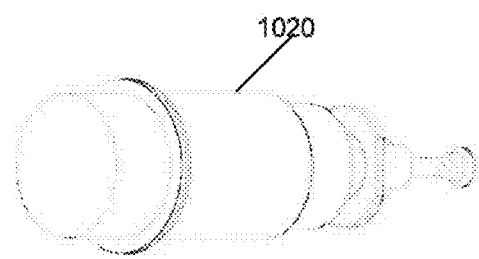
Figure 13B:
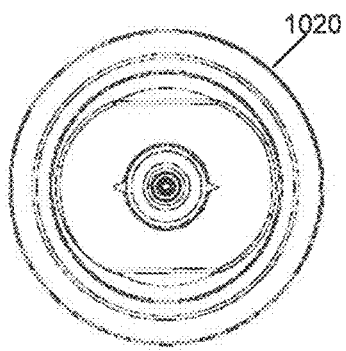
Figure 13E:
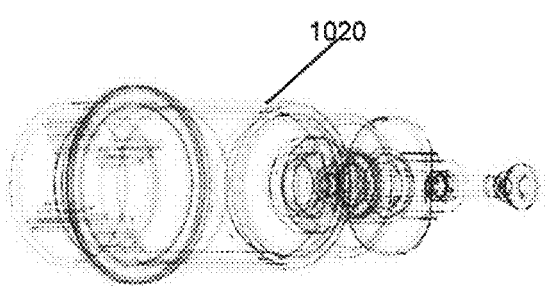
Figure 13C:
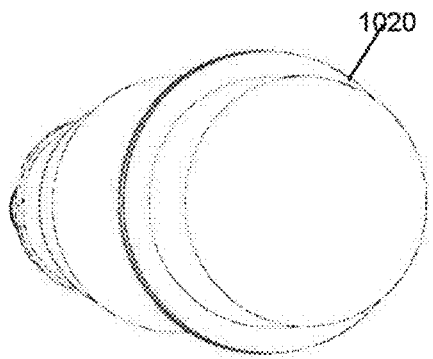
Figure 13F:
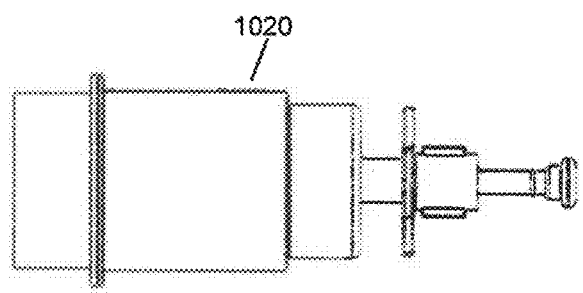

Holder cap 1920 is adapted to fit onto vial holder 1910. FIG. 12 shows holder cap 1920 in accordance with the invention. FIG. 12A shows a perspective view of a dissected holder cap 1920. FIG. 12B shows a cross-sectional view of holder cap 1920. FIG. 12C shows an end view of holder cap 1920. FIG. 12D shows an end view of holder cap 1920. FIG. 12E shows a perspective view of holder cap 1920. FIG. 12F shows a perspective view of holder cap 1920. FIG. 12G shows a side view of holder cap 1920. The holder cap element has an end base having a plurality of toothpick-like sticks or nails 1921 spaced apart thereby allowing fluidity of air, vapor or gas flow during a sterilization process of the drug vial container. Alternatively, the end base may have at least two flat pans crossing over perpendicularly to each other, each of the flat pans having orifices, thereby allowing fluidity of air, vapor or gas flow during a sterilization process of the drug vial container.

FIG. 13 shows connection port/vial holder apparatus 1020 in an assembled configuration in accordance with the invention. Connecting end 2005 of vial holder 1910 is connected to connector end 1605 of connection port 1510. FIG. 13A shows a cross-sectional view of connection port/vial holder apparatus 1020. FIG. 13B shows an end view of connection port/vial holder apparatus 1020. FIG. 13C shows an end view of connection port/vial holder apparatus 1020. FIGS. 13D and 13E shows perspective views of connection port/vial holder apparatus 1020. FIG. 13F shows a side view of connection port/vial holder apparatus 1020. Alternative connection port/vial holder apparatus 1020 can be assembled with using connection port 1510-1.

Figure 14A:
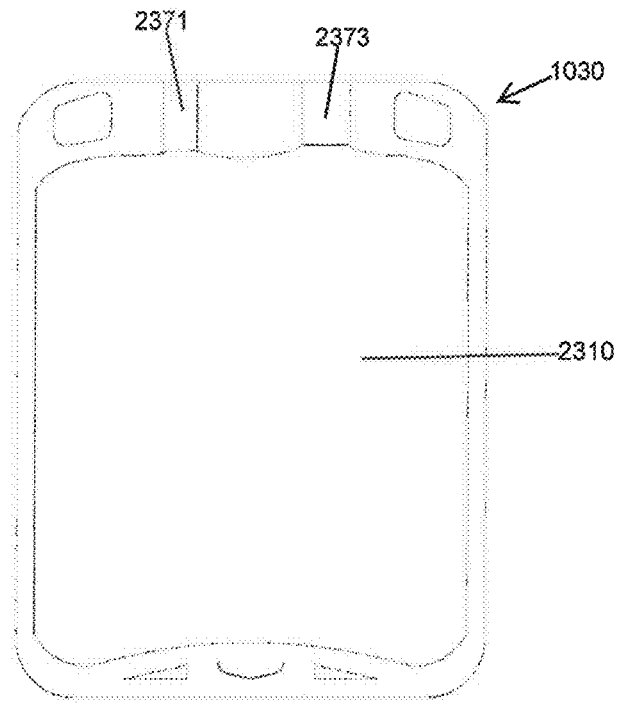
FIGS. 14A-14C show pouches of different size in accordance with the invention.
Figure 14B:
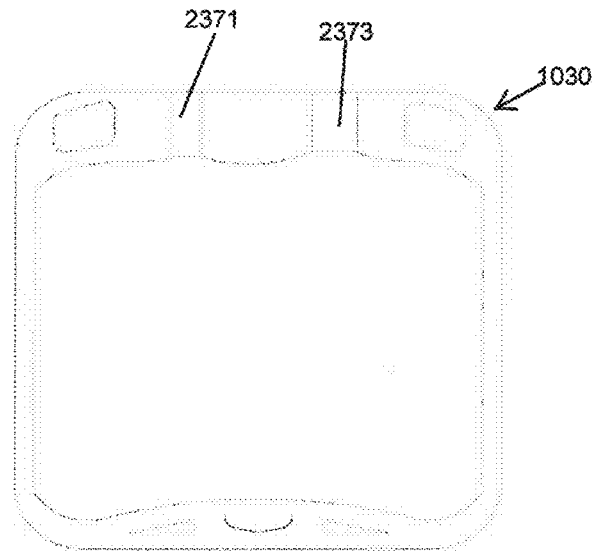
Figure 14C:
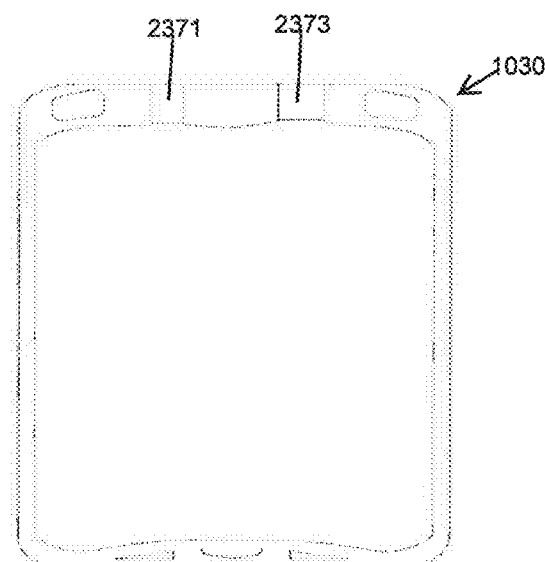

FIGS. 14A, 14B and 14C show pouch 1030, in different sizes, in accordance with the invention. Pouch 1030 includes a volume 2310, a first opening 2371 and a second opening 2373. Opening 2371 is adapted to receive releasing member 1010. Opening 2373 is adapted to receive connection port/vial holder apparatus 1020. The openings 2371 and 2373 are adapted to receive the appropriate element (releasing member 1010 or connection port/vial holder apparatus 1020) and is not limited to the arrangement as provided above.

FIG. 15 shows syringe kit 1000 in an assembled configuration. As shown in FIG. 15A, releasing member 1010 and connection port/vial holder apparatus 1020 are connected securely to pouch 1030 via openings 2371, 2373. FIG. 15B shows different views of the assembled syringe kit. FIG. 15C shows alternative arrangements of the releasing member 1010 and connection port/vial holder apparatus 1020 connected securely to the pouch 1030.

Figures 16A, 16B, 16C:
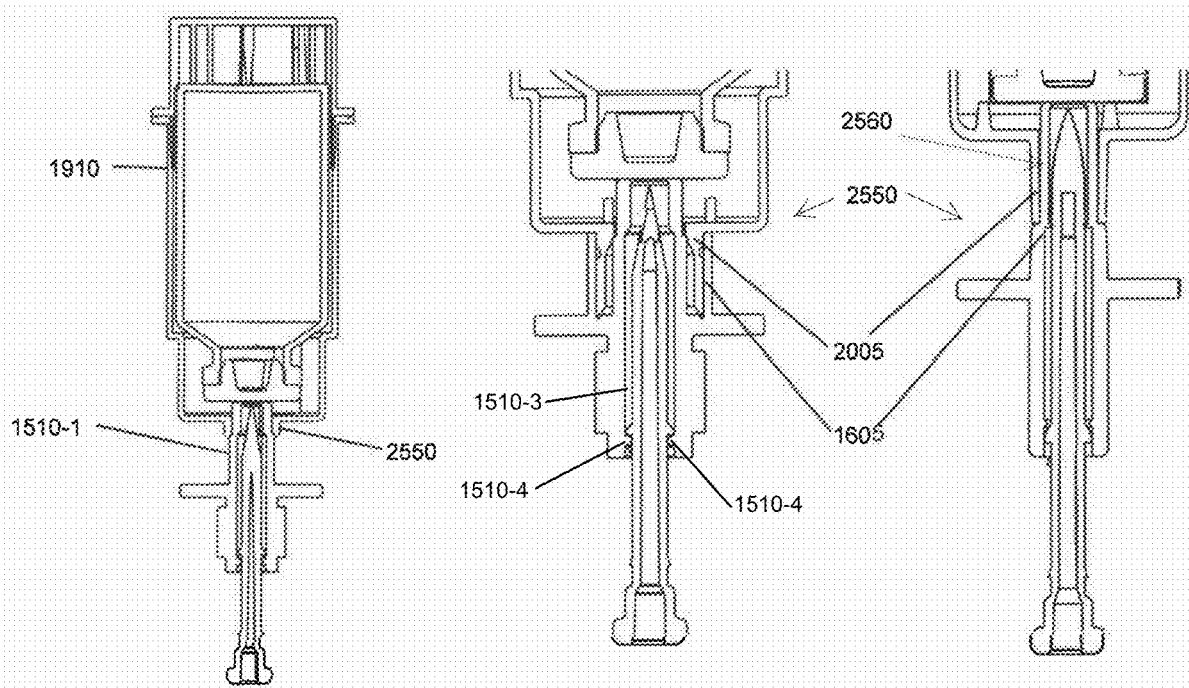
FIG. 16A-16C show a fused connection port connecting the drug vial holder and a liquid holding pouch in accordance with the invention.

In accordance with the invention illustrated by FIG. 16A, vial holder 1910 and connection port 1510-1 are fused together. Specifically, FIG. 16B shows connecting end 2005 of vial holder 1910 is fused to connector end 1605 of connection port 1510-1 to form fused connection 2550. FIG. 16C shows connecting end 2005 of vial holder 1910 is claimed to connector end 1605 of connection port 1510 and a tubular ring 2560 is sealing the connection. This design not only advantageously reduces the number of parts and therefore reduces manufacturing costs, but also maintains sterility of the entire internal communication between the drug vial container and the second container holding the liquid solution.

Additionally, the vial holder apparatus 1020 provides 100% sterility of the entire internal drug vial kit. The sterility can be confirmed by the hydrogen peroxide chemical indicator which confirms that the inside of the drug vial kit is secured from contamination entering the sterile environment.

Figures 17A, 17B:
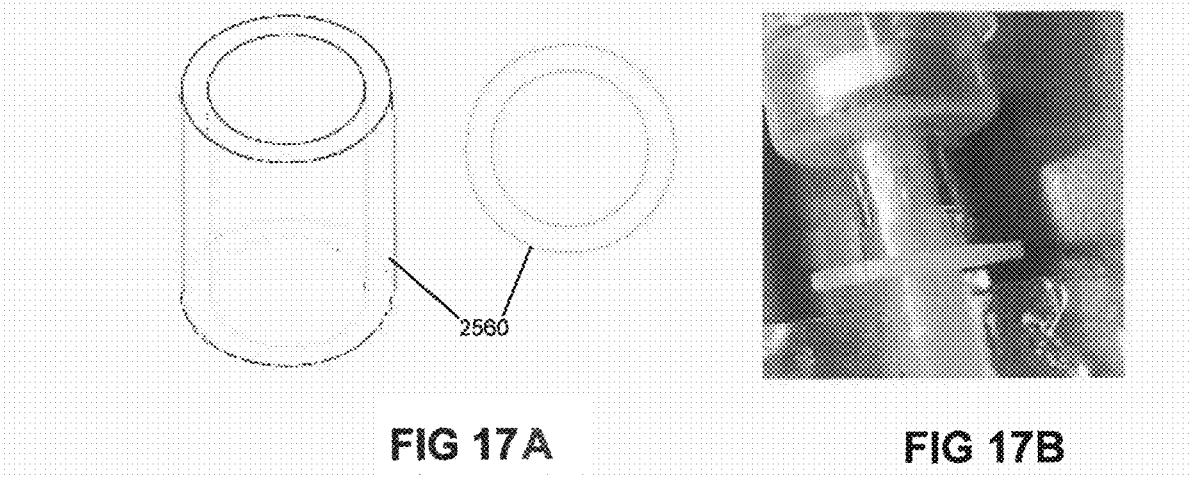
FIG. 17A-17B shows a tubular ring surrounding the connection between the vial holder and the infusion port.

In accordance with an embodiment illustrated by FIG. 17A shows a perspective and top view of a tubular ring 2560 surrounding the connection between the vial holder and the connection port. As shown in FIG. 16C, this tubular ring is configured to hug the connection between the vial holder and the connection port thereby further protecting the integrity and sterility of the system in accordance of the invention. The ring can be made of any material suitable for and used in the medical device industry, such as polyvinyl chloride (PVC), polypropylene (PP), polyethylene (PE), polystyrene (PS) as well as nylon, polyethylene terephthalate (PET), polyimide (PA), polycarbonate (PC), acrylonitrile butadiene (ABS), polyetheretherketone (PEEK) and polyurethane (PU). The most widely used plastic material in medical applications is PVC followed by PE, PP, PS and PET. PVC most widely used in pre-sterilized single use medical applications. FIG. 17B shows the tubular ring surrounding the connection between the vial holder and the infusion port.

Figure 18:
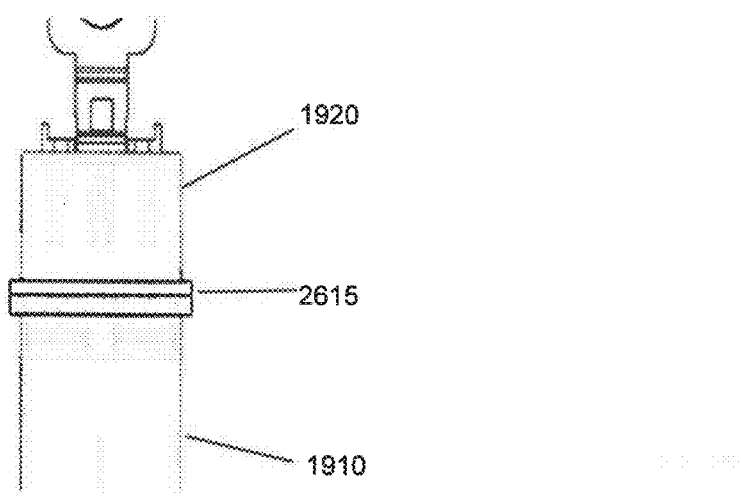
FIG. 18 shows a holder cap fused to a vial holder in accordance with an embodiment.

In accordance with an embodiment illustrated by FIG. 18 holder cap 1920 is fused to vial holder 1910 to form a fused joint 2615. This design advantageously reduces the number of parts and therefore reduces manufacturing costs.

Figure 19A:
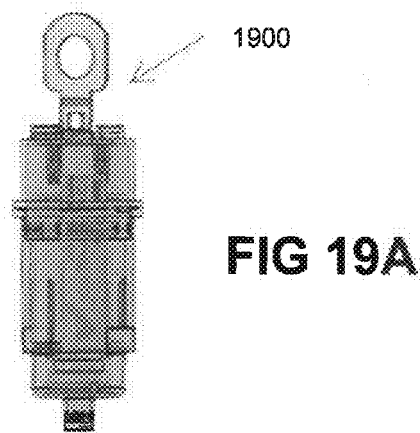
FIGS. 19A-19B shows a drug vial container with the hydrogen peroxide chemical indicator.
Figure 19B:
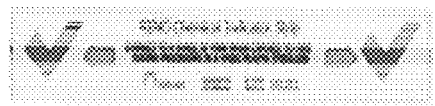

FIG. 19A shows a hydrogen peroxide chemical indicator inside the drug vial holder assembly 1900. FIG. 19B shows a close up of the hydrogen peroxide chemical indicator.

Thus, in accordance with an embodiment, an integrated injectable infusion is provided. The integrated injectable infusion includes In another embodiment, the vial holder element and the holder cap element are fused by heat sealing, by ultrasound welding, or by adhesives.

The foregoing embodiments are merely exemplary and are not to be construed as limiting the present invention. The description of the present invention is intended to be illustrative, and not to limit the scope of the claims. Many alternatives, modifications and variations will be apparent to those skilled in the art within the scope of the invention.

We claim:

1. An integrated injectable infusion system consisting of:
a drug vial container adapted to hold a drug vial, the drug vial container comprising a vial holder element and a holder cap element, and the vial holder element and the holder cap element are fused together forming a seal;
a second container adapted to hold a liquid, the second container including a first end and a second end;
a fused connection port having an upper end and a lower end, the upper end fused to the drug vial container and the lower end fused to the first end of the second container, the fused connection port consisting of a cavity and an internal surface extending from the upper end to the lower end, the lower end consisting of an opening having a first width, the internal surface consisting of a single internally protruding flange, the single internally protruding flange being an integral part of the internal surface of the cavity, wherein the cavity has a second width at a location of the single internally protruding flange, the second width being smaller than the first width of the opening;
a releasing member disposed at the second end of the second container, wherein the releasing member is adapted to release the liquid from the second container; and
a flue needle comprising a seat and a point, wherein the point of the flue needle is adapted to enter the cavity of the fused connection port and perforate the drug vial in response to a pressure applied on the seat of the flue needle, the flue needle further comprising:
at least two interrupting protuberances on an outer circumference of the flue needle, the interrupting protuberances configured for easy insertion and for preventing the flue needle from retracting after the pressure applied on the seat of the flue needle perforates the drug vial; and
at least one fixing protuberance on the outer circumference of the flue needle, parallel to the at least two interrupting protuberances, configured to contact and interact with the single internally protruding flange of the fused connection port, wherein contact between the at least one fixing protuberance and the single internally protruding flange of the fused connection port prevents the flue needle from moving from an initial position in the absence of an external force,
the releasing member consisting of an infusion port and a releasing cap, wherein the infusion port consists of an outlet fixed to the second container adapted to prevent leakage of liquids from the second container, a releasing extended rim is mounted at an inner end of the outlet and wherein the releasing cap covers the inner end of the outlet and exposing only a center of the releasing extended rim,
wherein the holder cap element comprises an end base having a plurality of toothpick-like sticks or nails spaced apart and allowing fluidity of air, vapor or gas flow during a sterilization process of the drug vial container, thereby sterilizing an inner cavity of the vial holder and the holder cap element and an outer surface of the drug vial container, and
wherein the system further comprising a tubular ring surrounding the connection between the vial holder and the fused connection port configured to further seal and protect the integrity of the system.

2. The integrated injectable infusion system of claim 1, wherein the drug vial contains a medicine selected from the group consisting of antibiotics, anticancer agents, broad spectrum penicillins, cephalosporins, macrolides, medium and narrow spectrum penicillins, aminoglycosides, carbenicillins, systemic antifungal agents, antitubercular agents, antiviral agents, anti-HIV agents, alkylating agents, antimetabolites, vinca alkaloids, antineoplastic antibiotics, platinum antineoplastics and a mixture thereof.

3. The integrated injectable infusion system of claim 1, wherein the drug vial contains a medicine and the medicine is an antibiotic or an anticancer agent.

4. The integrated infusion system of claim 3, wherein the medicine is selected from the group consisting of ceftriaxone, cefmetazole sodium, vacomycin hcl, cefotiam HCl, imipenem monohydrate, cilastatin sodium, cefoperazone sodium, sulbactam sodium, teicoplanin, cefotetan disodium, ceftizoxime sodium, ceftezole sodium, cefpiramide sodium, and fosfomycin.

5. The integrated infusion system of claim 3, wherein the medicine is selected from the group consisting of ceftriaxone 500 mg, ceftriaxone 1 g, ceftriaxone 2 g, cefmetazole sodium 1 g, cefmetazole sodium 0.5 g, vacomycin HCl 1 g, vacomycin HCl 500 mg, cefotiam HCl 1 g, cefotiam HCl 500 mg, imipenem monohydrate 0.5 g, cilastatin sodium 0.5 g, imipenem monohydrate 250 mg, cilastatin sodium 250 mg, cefoperazone sodium 500 mg, sulbactam sodium 500 mg, teicoplanin 0.2 g, cefotetan disodium 1 g, ceftizoxime sodium 1 g, ceftezole sodium 1 g, cefpiramide sodium 1 g, and fosfomycin 1 g.

6. The integrated injectable infusion system of claim 1, wherein the drug vial contains a medicine and is selected from the group consisting of aciclovir, amikacin sulfate, amoxicillin, amoxicillin, ampicillin, arbekacin, astromicin, azithromycin, aztreonam, belotecan, bendamustine, carbapenem, capreomycin, carboplatin, carumonam, cefamandole nafate, cefazolin, cefbuperazone, cefepime, cefmenoxime, cefmetazole, cefminox, cefodizime, cefonicid, cefoperazone, cefoperazone, ceforanide, cefotaxime, cefotetan, cefotiam, cefoxitn, cefpiramide, cefpirome, cefradine, ceftazidime, ceftezole, ceftizoxime, ceftriaxone, cefuroxime, cilastatin, cisplatin, clarithromycin, clavulanic acid, clindamycin phosphate, colistin sodium methanesulfonate, cyclophosphamide, cytarabine, dacarbazine, dalfopristin, doripenem monohydrate, decitabine, docetaxel, doxorubicin, enocitabine, ertapenem, etapenem, erythromycin lactobionate, etoposide, flomoxef sodium, fludarabine, fluorouracil, fosfomycin sodium, ganciclovir, gemcitabine, gentamicin sulfate, heptaplatin, idarubicin, ifosfamide, imipenem, irinotecan, isepamicin sulfate, latamoxef, lincomycin, mecillinam, melphalan, meropenem, methotrexate, micafungin, micronomicin sulfate, netilmicin, oxaliplatin, paclitaxel, panipenem, betamipron, pemetrexed, piperacillin, piperacillin, piperacillin, quinupristin, sisomicin, sulbactam, sulbenicillin, tazobactam, teicoplanin, thiotepa, ticarcillin, tobramycin, topotecan, ulbactam, vancomycin, vinblastine, vincristine, vinorelbine, voriconazole, a pharmaceutical salt thereof, and a mixture thereof.

7. The integrated infusion system of claim 1, wherein the number of interrupting protuberances on the flue needle is three.

8. The integrated infusion system of claim 1, wherein the flue needle is a cavity needle having at least one passage through which a liquid medicine flows.

9. The integrated infusion system of claim 1, wherein the drug vial is formed from one of a glass material and a plastic material.

10. The integrated infusion system of claim 1, wherein the second container is formed from a plastic material.

11. The integrated infusion system of claim 1, wherein the vial holder element and the holder cap element are fused by heat sealing, by ultrasound welding, or by adhesives.

12. An integrated injectable infusion system consisting of:
   a drug vial container adapted to hold a drug vial, the drug vial container comprising consisting of a vial holder element and a holder cap element, and the vial holder element and the holder cap element are fused together forming a seal;
   a hydrogen peroxide chemical indicator inside the drug vial container for visual sterility verification;
   a second container adapted to hold a liquid, the second container including a first end and a second end;
   a fused connection port having an upper end and a lower end, the upper end fused to the drug vial container and the lower end fused to the first end of the second container, the fused connection port consisting of a cavity and an internal surface extending from the upper end to the lower end, the lower end consisting of an opening having a first width, the internal surface consisting of a single internally protruding flange, the single internally protruding flange being an integral part of the internal surface of the cavity, wherein the cavity has a second width at a location of the single internally protruding flange, the second width being smaller than the first width of the opening;
   a releasing member disposed at the second end of the second container, wherein the releasing member is adapted to release the liquid from the second container; and
   a flue needle comprising a seat and a point, wherein the point of the flue needle is adapted to enter the cavity of the fused connection port and perforate the drug vial in response to a pressure applied on the seat of the flue needle, the flue needle further comprising:
      at least three interrupting protuberances on the flue needle, the interrupting protuberances being configured for easy insertion and for preventing the flue needle from retracting after the pressure applied on the seat of the flue needle perforates the drug vial;
      at least one fixing protuberance configured to contact and interact with the single internally protruding flange of the fused connection port, wherein contact between the at least one fixing protuberance and the single internally protruding flange of the fused connection port prevents the flue needle from moving from an initial position in the absence of an external force,
   the releasing member consisting of an infusion port and a releasing cap, wherein the infusion port consists of an outlet fixed to the second container adapted to prevent leakage of liquids from the second container, a releasing extended rim is mounted at an inner end of the outlet and wherein the releasing cap covers the inner end of the outlet and exposing only a center of the releasing extended rim,
   wherein the holder cap element comprises an end base having a plurality of toothpick-like sticks or nails spaced apart and allowing fluidity of air, vapor or gas flow during a sterilization process of the drug vial container, thereby sterilizing an inner cavity of the vial holder and the holder cap element and an outer surface of the drug vial container,
   wherein the drug vial contains a medicine and the medicine is an antibiotic or an anticancer agent, and
   wherein the system further comprises tubular ring surrounding the connection between the vial holder and the fused connection port configured to further seal and protect the integrity of the system.

* * * * *